(12) United States Patent
Lee et al.

(10) Patent No.: US 7,826,901 B2
(45) Date of Patent: Nov. 2, 2010

(54) GENERATION OF THERAPY PROGRAMS AND PROGRAM GROUPS

(75) Inventors: Michael T. Lee, Minnetonka, MN (US); Steven M. Goetz, Brooklyn Center, MN (US); Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1301 days.

(21) Appl. No.: 10/831,971

(22) Filed: Apr. 26, 2004

(65) Prior Publication Data

US 2004/0267330 A1 Dec. 30, 2004

Related U.S. Application Data

(63) Continuation-in-part of application No. 10/424,194, filed on Apr. 25, 2003, now Pat. No. 7,463,928.

(51) Int. Cl.
*A61N 1/00* (2006.01)
(52) U.S. Cl. .............................. 607/59; 607/30; 607/31; 607/32; 607/60; 128/903
(58) Field of Classification Search ....................... None
See application file for complete search history.

(56) References Cited

U.S. PATENT DOCUMENTS

| | | | |
|---|---|---|---|
| 4,515,158 A | | 5/1985 | Patrick et al. |
| 4,549,548 A | | 10/1985 | Wittkampf et al. |
| 4,823,808 A | | 4/1989 | Clegg et al. |
| 5,033,469 A | | 7/1991 | Brodard |
| 5,443,486 A | * | 8/1995 | Hrdlicka et al. ............... 607/59 |
| 5,690,691 A | | 11/1997 | Chen et al. |
| 5,775,331 A | | 7/1998 | Raymond et al. |
| 5,893,883 A | | 4/1999 | Torgerson et al. |

(Continued)

FOREIGN PATENT DOCUMENTS

EP 0 730 882 9/1996

(Continued)

OTHER PUBLICATIONS

International Search Report and Written Opinion for PCT/US2004/002155, filed Jan. 27, 2004.

(Continued)

*Primary Examiner*—Carl H Layno
*Assistant Examiner*—Yun Haeng Lee
(74) *Attorney, Agent, or Firm*—Shumaker & Sieffert, P.A.

(57) ABSTRACT

A programmer allows a clinician to identify desirable combinations of electrodes from within an electrode set implanted in a patient that enable delivery of desirable neurostimulation therapy by an implantable medical device. The clinician may create neurostimulation therapy programs that include identified desirable electrode combinations. In some embodiments, the clinician may use the programmer to select a program, such as a program identified during a neurostimulation programming session, and direct the programmer to replicate the selected program. The programmer may change one or more parameters of the selected program, such as pulse amplitude or duty cycle, when generating the copy of the selected program. In some embodiments, the programmer may associate each of a plurality of programs identified during a neurostimulation therapy programming session with one or more program categories, and may automatically generate program groups that include two or more of the programs based on the program categories.

31 Claims, 12 Drawing Sheets

U.S. PATENT DOCUMENTS

| | | | |
|---|---|---|---|
| 5,938,690 | A | 8/1999 | Law et al. |
| 6,044,303 | A | 3/2000 | Agarwala et al. |
| 6,052,624 | A | 4/2000 | Mann |
| 6,234,964 | B1 | 5/2001 | Iliff |
| 6,238,423 | B1 | 5/2001 | Bardy |
| 6,393,325 | B1 | 5/2002 | Mann et al. |
| 6,440,090 | B1 | 8/2002 | Schallhorn |
| 6,473,653 | B1 | 10/2002 | Schallhorn et al. |
| 6,480,743 | B1 | 11/2002 | Kirkpatrick et al. |
| 6,516,227 | B1 | 2/2003 | Meadows et al. |
| 6,587,724 | B2 | 7/2003 | Mann |
| 6,622,048 | B1 | 9/2003 | Mann et al. |
| 6,735,477 | B2 | 5/2004 | Levine |
| 6,889,076 | B2 | 5/2005 | Cigaina |
| 7,146,223 | B1 | 12/2006 | King |
| 7,313,440 | B2 | 12/2007 | Miesel |
| 2001/0049542 | A1 | 12/2001 | Florio et al. |
| 2002/0035384 | A1 | 3/2002 | Fox et al. |
| 2002/0072780 | A1 | 6/2002 | Foley |
| 2002/0116036 | A1 | 8/2002 | Daignault, Jr. et al. |
| 2002/0169484 | A1 | 11/2002 | Mathis et al. |
| 2003/0004549 | A1 | 1/2003 | Hill et al. |
| 2003/0036783 | A1 | 2/2003 | Bauhahn et al. |
| 2004/0041352 | A1 | 3/2004 | Hohe et al. |
| 2004/0138711 | A1 | 7/2004 | Osorio et al. |
| 2004/0147816 | A1 | 7/2004 | Policker et al. |
| 2004/0158298 | A1* | 8/2004 | Gliner et al. .................. 607/48 |
| 2004/0181262 | A1 | 9/2004 | Bauhahn |
| 2004/0267330 | A1 | 12/2004 | Lee et al. |
| 2005/0060009 | A1 | 3/2005 | Goetz |
| 2005/0149142 | A1 | 7/2005 | Starkebaum |
| 2005/0209050 | A1 | 9/2005 | Bartels |
| 2005/0222638 | A1 | 10/2005 | Foley et al. |
| 2006/0036293 | A1 | 2/2006 | Whitehurst et al. |
| 2006/0074459 | A1 | 4/2006 | Flesler et al. |

FOREIGN PATENT DOCUMENTS

| | | |
|---|---|---|
| EP | 1 249 254 | 10/2002 |
| EP | 1 304 137 | 4/2003 |
| WO | WO 01/83028 | 11/2001 |
| WO | WO 01/93953 | 12/2001 |
| WO | WO 02/09808 | 2/2002 |
| WO | WO 2004/041352 | 5/2004 |
| WO | WO/2007/117348 A1 | 10/2007 |

OTHER PUBLICATIONS

International Search Report and Written Opinion for PCT/US2004/012838, filed Apr. 26, 2004.

Written Opinion dated Mar. 30, 2005, International Application No. PCT/US2004/012838.

Notification of Transmittal of the International Preliminary Report on Patentability for PCT/US2004/002155 dated Jun. 30, 2005 (8 pgs.).

Notification of Transmittal of the International Preliminary Report on Patentability for PCT/US2004/012838 dated Aug. 30, 2005 (9 pgs.).

Final Office Action for U.S. Appl. No. 11/698,655, mailed Nov. 2, 2009, 8 pages.

Response to Final Office Action for U.S. Appl. No. 11/698,655, filed Dec. 29, 2009, 12 pages.

Advisory Action for U.S. Appl. No. 11/698,655, mailed Jan. 19, 2010, 3 pages.

Office Action dated Apr. 4, 2008 for U.S. Appl. No. 11/402,652, (18 pages).

Response to Office Action dated Jul. 3, 2008 for U.S. Appl. No. 11/402,652, (10 pages).

Office Action dated Sep. 17, 2008 for U.S. Appl. No. 11/402,652, 16 pgs.

Responsive Amendment dated Nov. 17, 2008 for U.S. Appl. No. 11/402,652, 15 pgs.

Responsive Amendment dated Jan. 6, 2010 for U.S. Appl. No. 11/402,652, 18 pgs.

Office Action dated Oct. 6, 2009 for U.S. Appl. No. 11/402,652, 10 pgs.

Responsive Amendment dated May 1, 2009 for U.S. Appl. No. 11/402,652, 14 pgs.

Office Action dated Feb. 2, 2009 for U.S. Appl. No. 11/402,652, 9 pgs.

Responsive Amendment dated Sep. 21, 2009 for U.S. Appl. No. 11/402,652, 10 pgs.

Office Action dated Jul. 27, 2009 for U.S. Appl. No. 11/402,652, 10 pgs.

Office Action dated Dec. 28, 2009 for U.S. Appl. No. 11/402,657. 7 pgs.

Responsive Amendment dated Mar. 26, 2010 for U.S. Appl. No. 11/402,657, 16 pgs.

Office Action dated Mar. 12, 2010 for U.S. Appl. No. 11/404,069, 9 pgs.

Responsive Amendment dated Jun. 3, 2010 for U.S. Appl. No. 11/404,069, 14 pgs.

Final Office Action for U.S. Appl. No. 11/402,657, mailed Jun. 24, 2010, 12 pages.

Response to Final Office Action for U.S. Appl. No. 11/402,657, filed Aug. 20, 2010, 10 pages.

* cited by examiner

FIG. 6A (120)

| 12 | 13 |
|----|----|
| 8  | 9  |
| 4  | 5  |
| –  | 1  |
| 2  | 3  |
| 6  | 7  |
| 10 | 11 |
| 14 | 15 |

FIG. 6B (130)

| 13 | 12 |
|----|----|
| 9  | 8  |
| 5  | 4  |
| 1  | –  |
| 3  | 2  |
| 7  | 6  |
| 11 | 10 |
| 15 | 14 |

FIG. 6C (140)

| 6 |
|---|
| 4 |
| 2 |
| – |
| 1 |
| 3 |
| 5 |
| 7 |

FIG. 6D (150)

| 13 | 14 |
|----|----|
| 9  | 10 |
| 5  | 6  |
| +  | 4  |
| –  | 3  |
| 1  | 2  |
| 7  | 8  |
| 11 | 12 |

FIG. 6E (160)

| 11 | 12 |
|----|----|
| 7  | 8  |
| 1  | 2  |
| −  | 3  |
| +  | 4  |
| 5  | 6  |
| 9  | 10 |
| 13 | 14 |

FIG. 6F (170)

| 5 |
|---|
| 3 |
| 1 |
| − |
| + |
| 2 |
| 4 |
| 6 |

FIG. 6G (180)

| 6 |
|---|
| 4 |
| 2 |
| + |
| − |
| 1 |
| 3 |
| 5 |

FIG. 6H (190)

|   | 11 |
|---|----|
|   | 10 |
|   | 7  |
| + | 4  |
| − | 3  |
| 1 | 2  |
| 5 | 6  |
| 8 | 9  |

200

| | |
|---|---|
| 11 | 10 |
| 7 | 6 |
| 4 | 2 |
| − | + |
| 3 | 1 |
| 8 | 5 |
| 12 | 9 |
| 14 | 13 |

| | |
|---|---|
|  | 11 |
|  | 8 |
| + | 5 |
|  | 4 |
| − | 3 |
| 1 | 2 |
| 6 | 7 |
| 9 | 10 |

| |
|---|
| 3 |
| 2 |
| 1 |
| − |
| + |
|  |
|  |
|  |

FIG. 6K

GENERATION OF THERAPY PROGRAMS AND PROGRAM GROUPS

This application is a continuation-in-part of U.S. application Ser. No. 10/424,194, filed Apr. 25, 2003, now U.S. Pat. No. 7,463,928 the entire content of which is incorporated herein by reference.

TECHNICAL FIELD

The invention relates to neurostimulation therapy and, more particularly, to generation of therapy programs and program groups used for delivery of neurostimulation therapy to a patient.

BACKGROUND

Implantable medical devices may be used to deliver neurostimulation therapy to patients to treat a variety of symptoms or conditions such as chronic pain, tremor, Parkinson's disease, epilepsy, incontinence, or gastroparesis. An implantable medical device may deliver neurostimulation therapy via leads that include electrodes located proximate to the spinal cord, pelvic nerves, or stomach, or within the brain of a patient. In general, the implantable medical device delivers neurostimulation therapy in the form of electrical pulses.

A clinician may select values for a number of programmable parameters in order to define the neurostimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient. The clinician may also select as parameters particular electrodes within an electrode set to be used to deliver the pulses, and the polarities of the selected electrodes. A group of parameter values may be referred to as a program in the sense that they drive the neurostimulation therapy to be delivered to the patient.

The process of selecting values for the parameters that provide adequate results can be time consuming, and may require a great deal of trial and error before a "best" program is discovered. The "best" program may be a program that is better in terms of clinical efficacy versus side effects experienced and power consumption than other programs tested. As a portion of the overall parameter selection process, the process of selecting electrodes and the polarities of the electrodes can be particularly time-consuming and tedious. The clinician may need to test all possible combinations of electrodes within the set implanted in the patient, or a significant portion thereof, in order to identify a "best" combination of electrodes and their polarities.

In some cases, the clinician may test combinations by manually specifying each combination to test based on intuition or some idiosyncratic methodology, and recording notes on the efficacy and side effects of each combination after delivery of stimulation via that combination. In this manner, the clinician is able to later compare and select from the tested combinations. As an example illustrating the magnitude of such a task, implantable medical devices commonly deliver spinal cord stimulation therapy (SCS) to a patient via two leads that include eight electrodes per lead and provide well over one million potential electrode combinations.

SUMMARY

In general, the invention is directed to techniques that may be employed by a programming device to allow a clinician or patient to identify combinations of electrodes from within an electrode set implanted in a patient that enable delivery of desirable neurostimulation therapy by an implantable medical device. The programmer may execute an electrode combination search algorithm to select combinations of electrodes to test in a non-random order. By selecting combinations in a non-random order, the programmer may allow the clinician or patient to more quickly identify desirable electrode combinations.

According to algorithms consistent with the invention, the programmer may identify a position of a first cathode electrode for subsequent combinations, and then select electrodes from the electrode set to test with the first cathode as anodes or additional cathodes based on the proximity of the electrodes to the first cathode. The programmer may identify a first position within the electrode set, which may be a central position within the electrode set, and control the implantable medical device to test the electrode located at that position as the first cathode. The programmer may then test additional electrodes from within the set as the first cathode in an order based on proximity to the first cathode.

The programmer may receive input from the clinician or patient indicating which tested electrode is the first cathode, and then control the implantable medical device to test other electrodes of the set in combination with the first cathode. Undesignated electrodes may be tested as anodes and additional cathodes in an order based on proximity to the first cathode. In some cases, only a subset of the undesignated electrodes may be tested to avoid testing redundant electrode combinations, i.e., electrode combinations that would produce substantially the same current flow as an electrode combination already tested.

The programmer may store information for each combination tested, and the information may facilitate the identification of desirable electrode combinations by the clinician. For example, the programmer may present a list of tested combinations and their associated information, and the list may be ordered according to the information. The clinician may create neurostimulation therapy programs that include identified desirable program combinations.

For example, after identifying a plurality of desirable electrode combinations, the clinician or patient may use the programmer to test a variety of values of other neurostimulation therapy program parameters, such as pulse amplitude, pulse rate, pulse width and duty cycle, with the identified electrode combinations, i.e., to test a variety of neurostimulation therapy programs. The programmer may collect rating information for each of the tested neurostimulation therapy programs. The clinician may use the programmer to identify a plurality of desirable neurostimulation therapy programs from among those tested during the programming session for use in controlling delivery of neurostimulation therapy to the patient by the implantable medical device.

In some embodiments, the programmer provides a neurostimulation therapy program replication function. In such embodiments, the programmer selects one of the neurostimulation therapy programs identified during the programming session, e.g., receives a selection of one of the programs made by the clinician, and receives a replication command from the clinician. In response to the replication command, the programmer generates one or more copies of the selected neurostimulation therapy program. In some embodiments, as part of generation of a copy, the programmer may change one or more of the parameters of the selected program, e.g., pulse amplitude, pulse rate, pulse width, duty cycle, or electrode combination. In other embodiments, the programmer may provide one or more copies that are identical to the selected program, and the patient or clinician may adjust one or more parameters of the copies.

In some embodiments, the implantable medical device delivers therapy to the patient according to program groups, i.e., groups of two or more neurostimulation therapy programs. The implantable medical device may deliver the two or more programs of a program group to the patient substantially simultaneously. For example, the implantable medical device may deliver each neurostimulation therapy pulse according to a different one of the plurality of programs of a program group.

In such embodiments, the programmer may automatically generate one or more program groups that include two or more of a plurality of neurostimulation programs identified as desirable during programming session. In particular, the programmer may associate each of a plurality of identified neurostimulation therapy programs with one or more of a plurality of program categories, and may generate the groups, e.g., assign programs to groups, based on their associated program categories. The programmer may automatically generate the program groups in response to receiving a program group generation command from the clinician.

Each of the program categories is related to a characteristic of neurostimulation therapy programs. For example, the programmer may categorize a neurostimulation therapy program by paresthesia location, e.g., left-side, right-side, or bilateral, or based on the location of electrodes included within its electrode combination. Generally, in embodiments in which neurostimulation therapy programs are categorized by paresthesia or electrode location, the programmer may generate a program group to include programs associated with different categories, e.g., programs associated with different paresthesia or electrode locations. A program group that includes programs associated with different paresthesia or electrode locations may be able to, for example, address complex pain patterns, and avoid conflicts that can arise when sequential pulses are delivered according to different programs via the same electrodes.

As other examples, the programmer may categorize a neurostimulation therapy program according to stimulation intensity, e.g., high, medium or low, according to posture, e.g., standing or sitting, according to patient activity, e.g., running or sitting, according to time of day, e.g., daytime or evening, according to symptom intensity, e.g., high or low, or according to stimulation side effects, e.g., high or low. Generally, in embodiments in which neurostimulation therapy programs are categorized by intensity, posture, activity, time of day, symptom intensity, or side effects, the programmer may generate a program group to include programs associated with the same category, e.g., programs associated with the same intensity, posture, activity, time of day, symptom intensity, or side effects. A program group that includes programs associated with the same stimulation intensity level, symptom intensity level, posture, or activity, for example, may be selected by the patient to address a current symptom level, or when the patient assumes a particular posture or undertakes a particular activity.

In exemplary embodiments, the programmer combinatorially generates program groups from a set of neurostimulation therapy programs identified during a programming session. In other words, the programmer may automatically generate a plurality of program groups by generating multiple combinations of neurostimulation therapy programs that comply with one or more criteria related to program categories. In some embodiments, the programmer may order the programs within each category according to rating information, e.g., collected during a neurostimulation programming session, and may maintain a preference for use of more "highly" rated programs when combining programs to create groups, e.g., may create program groups based on both the program categories and the rating information. For example, the programmer may exclude "poorly" rated programs from program groups, or may assign higher rated programs to groups more frequently than lower rated programs.

In one embodiment, the invention is directed to a method in which a first electrode of a set of electrodes implanted in a patient is selected to be included in a combination of electrodes for use in delivery of neurostimulation to the patient. The first electrode may be a cathode for the combination. A sequence of additional electrodes of the set to test for inclusion in the combination is automatically selected according to locations of the additional electrodes relative to the first electrode. The additional electrodes may be tested for inclusion of one of the additional electrodes as an anode for the combination.

In another embodiment, the invention is directed to a computer-readable medium containing instructions. The instructions cause a programmable processor to select a first electrode of a set of electrodes implanted in a patient to include in a combination of electrodes for use in delivery of neurostimulation to the patient. The instructions also cause a processor to automatically select a sequence of additional electrodes within the set to test for inclusion in the combination according to locations of the additional electrodes relative to the first electrode.

In another embodiment, the invention is directed to a device that includes a processor. The processor selects a first electrode of a set of electrodes implanted in a patient to include in a combination of electrodes for delivery of neurostimulation therapy to the patient. The processor also automatically selects a sequence of additional electrodes to test for inclusion in the combination according to locations of the additional electrodes relative to the first electrode. The device may be a programming device associated with one of a clinician and the patient.

In another embodiment, the invention is directed to a method in which a search algorithm is executed to control an implantable medical device to test combinations of electrodes in an order that is based on the proximity of the electrodes of the combinations to a central position within the set. Information identifying at least one of the tested combinations is stored as part of a neurostimulation therapy program that defines neurostimulation therapy to be delivered to the patient by the implantable medical device.

In another embodiment, the invention is directed to a method in which a neurostimulation therapy program that includes a set of neurostimulation therapy parameters is selected, and a replication command is received from a user. A copy of the selected neurostimulation therapy program is generated in response to the replication command, and the selected neurostimulation therapy program and the copy are provided to at least one of a programming device or a medical device. A selected one or more of the neurostimulation therapy program and the copy controls delivery of neurostimulation therapy to a patient by the medical device.

In another embodiment, the invention is directed to a device that includes a user interface, a communication circuit, and a processor. The processor selects a neurostimulation therapy program that includes a set of neurostimulation therapy parameters, receives a replication command from a user via the user interface, generates a copy of the selected neurostimulation therapy program in response to the replication command, and provides the selected neurostimulation therapy program and the copy to at least one of a programming device or a medical device via the communication circuit. A selected one or more of the neurostimulation therapy program and the copy controls delivery of neurostimulation therapy to a patient by the medical device.

In another embodiment, the invention is directed to a computer-readable medium comprising instructions. The instructions cause a programmable processor to select a neurostimulation therapy program that includes a set of neurostimulation therapy parameters, receive a replication command from a user, generate a copy of the selected neurostimulation therapy program in response to the replication command, and provide the selected neurostimulation therapy program and the copy to at least one of a programming device or a medical device. A selected one or more of the neurostimulation therapy program and the copy controls delivery of neurostimulation therapy to a patient by the medical device.

In another embodiment, the invention is directed to a method in which a plurality of neurostimulation therapy programs are identified during a neurostimulation therapy programming session, and each of the identified neurostimulation therapy programs is associated with at least one of a plurality of program categories. Each of the program categories is related to a characteristic of at least one of the identified neurostimulation therapy programs. A plurality of program groups is automatically generated based on the program categories, each of the program groups including at least two of the identified neurostimulation therapy programs.

In another embodiment, the invention is directed to a device that includes a memory and a processor. The memory stores a plurality of neurostimulation therapy programs identified during a neurostimulation therapy programming session. The processor associates each of the identified neurostimulation therapy programs with at least one of a plurality of program categories, and automatically generates a plurality of program groups based on the program categories. Each of the program categories is related to a characteristic of at least one of the identified neurostimulation therapy programs, and each of the program groups including at least two of the identified neurostimulation therapy programs In another embodiment, the invention is directed to a computer-readable medium comprising instructions. The instructions cause a programmable processor to identify a plurality of neurostimulation therapy programs during a neurostimulation therapy programming session, associate each of the identified neurostimulation therapy programs with at least one of a plurality of program categories, and automatically generate a plurality of program groups based on the program categories. Each of the program categories is related to a characteristic of at least one of the identified neurostimulation therapy programs, and each of the program groups including at least two of the identified neurostimulation therapy programs.

The invention may provide a number of advantages. For example, the invention may allow a clinician to more quickly identify desirable electrode combinations, reducing the overall amount of time the clinician spends programming neurostimulation therapy for a patient. In contrast to existing neurostimulation programming systems that present electrode combinations in a random order and idiosyncratic search methodologies employed by clinicians, programmer according to the invention may select electrode combinations in a systematic manner to test in an order such that electrode combinations that are more likely to enable desirable therapy are selected earlier in the search. Consequently, the clinician may be able to end the search before all potential electrode combinations have been tested if one or more desirable combinations have already been identified.

Even if a clinician elects to test all potential electrode combinations, e.g., if the electrode set is small enough to make testing all electrode combinations practical, the invention may reduce the time required to identify desirable electrode combinations by automating selection of each new combination to test. The invention may also avoid testing redundant combinations, i.e., combinations that are substantially equivalent to combinations already tested. Avoiding redundant combinations may further reduce the amount of time required for the search.

Additionally, the invention may improve the search process by collecting amplitude information, and rating information that is entered by the clinician or patient, for each combination tested. A programmer according to the invention may present a list of tested electrode combinations to the clinician, ordered according to one or both of the amplitude and rating information, allowing the clinician to more easily identify and select desirable combinations. A bracket of untested electrode combinations that are similar to identified electrode combinations may be used to create programs that are provided to the patient. Providing bracket programs to the patient allows the patient to experiment with the programs to "finely tune" the neurostimulation therapy provided by the implantable medical device without requiring the clinician to be involved.

By replicating a neurostimulation therapy program that has been identified as desirable, a programmer according to the invention may allow a clinician to quickly generate a plurality of similarly desirable programs for selection, modification and use by a patient. In embodiments in which the programmer changes one or more of pulse amplitude, pulse width, pulse rate, or duty cycle, the programmer may provide a plurality of similar programs with various intensities and battery consumption rates, e.g., a high intensity and low intensity version of a selected program. By providing a plurality of programs that are replicated with parameters that are changed in this manner, the programmer may enable selection of a program that addresses a current symptom level, e.g., a pain level which may vary based on patient posture, activity or time of day, with a comparatively lower rate of battery consumption. In some embodiments, the programmer may associate the selected program and the copies with respective postures, activities, times of day, symptom states, or side effect states, e.g., may label a selected program and a copy as "sitting" and "standing," "high" and "low," or "daytime" and "nighttime," respectively. In embodiments in which the programmer generates identical copies of a selected neurostimulation therapy program, the patient may use a patient programmer to adjust parameters of program copies to create similarly desirable programs with different intensities and battery consumption rates to, for example, address different symptom levels associated with different postures or activities.

As another example, by providing for automatic generation of program groups, a programmer according to the invention may be able to quickly provide a clinician with a plurality of program groups that include combinations of neurostimulation therapy programs. Moreover, use of program categories may allow the programmer to generate programs groups that include desirable and/or logical combinations of programs.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 6A-6K are diagrams illustrating example matrices that illustrate positions within exemplary electrode set configurations and orders in which electrodes within such electrode sets may be tested according to electrode combination search algorithms consistent with the invention.

DETAILED DESCRIPTION

Figure 1:
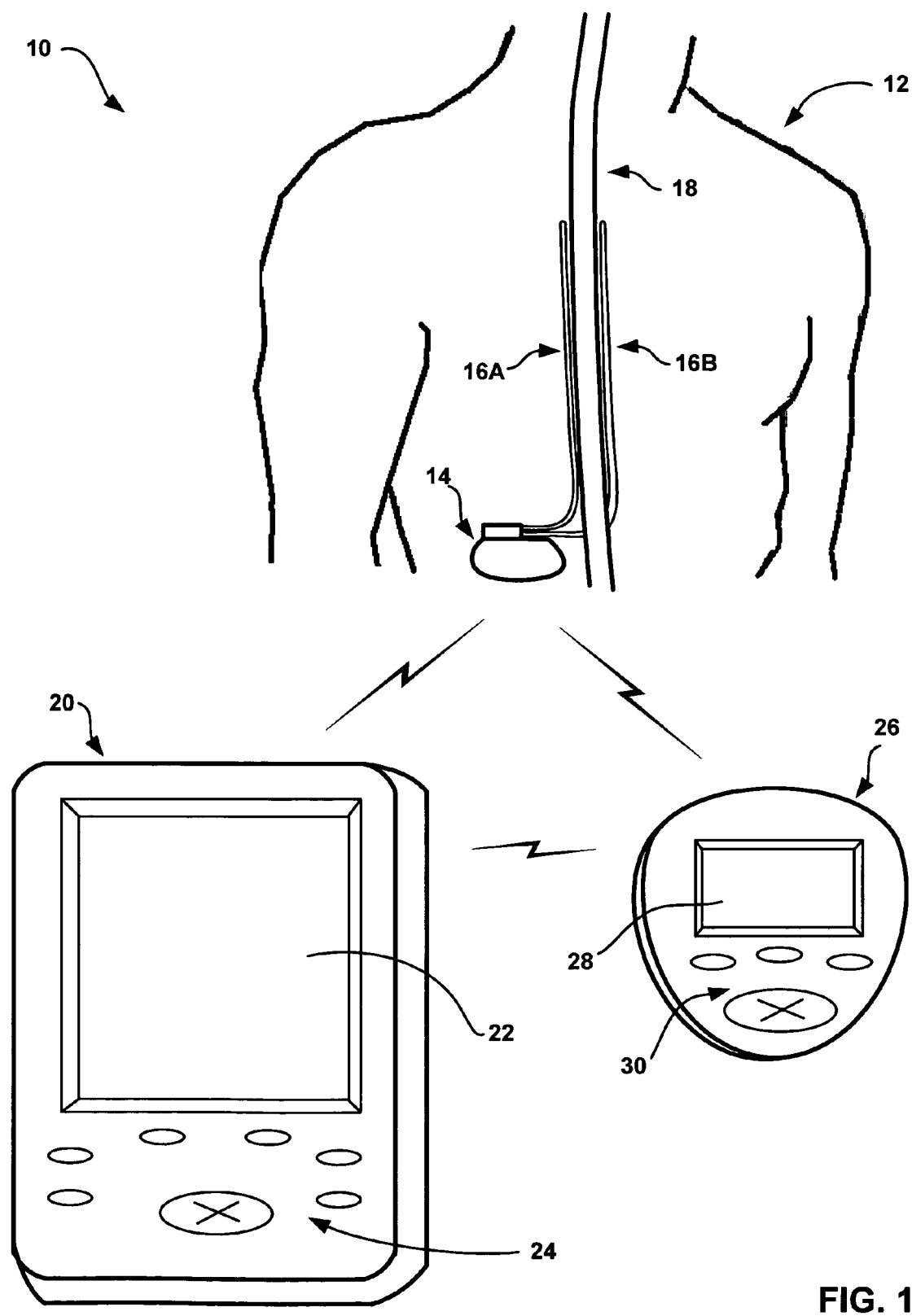
FIG. 1 is a diagram illustrating an example system for programming and delivering neurostimulation therapy.

FIG. 1 is a diagram illustrating an example system 10 for programming neurostimulation therapy for and delivering neurostimulation therapy to a patient 12. System 10 includes an implantable medical device 14 that delivers neurostimulation therapy to patient 12. IMD 14 may be an implantable pulse generator, and may deliver neurostimulation therapy to patient 12 in the form of electrical pulses. In the illustrated example system 10, IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12.

However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence or gastroparesis. Moreover, the invention is not limited to systems in which an IMD delivers neurostimulation therapy to patient 12. For example, in some embodiments of the invention, an external neurostimulator, e.g., a transcutaneous electrical stimulation (TENS) device, or a trial neurostimulator may deliver neurostimulation therapy to patient 12.

IMD 14 delivers neurostimulation therapy to patient 12 according to one or more neurostimulation therapy programs. A neurostimulation therapy program may include values for a number of parameters, and the parameter values define the neurostimulation therapy delivered according to that program. In embodiments where IMD 14 delivers neurostimulation therapy in the form of electrical pulses, the parameters may include pulse voltage or current amplitudes, pulse widths, pulse rates, duty cycles and the like. Further, each of leads 16 includes electrodes (not shown in FIG. 1), and the parameters for a program may include information identifying which electrodes have been selected for delivery of pulses according to the program, and the polarities of the selected electrodes.

A selected subset of the electrodes located on leads 16 and the polarities of the electrodes of the subset collectively define an "electrode combination." Electrode combinations refer to combinations of single or multiple cathode electrodes and single or multiple anode electrodes. Stimulation current flows between the cathodes and anodes for delivery of neurostimulation therapy.

System 10 also includes a clinician programmer 20. Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions. A clinician (not shown) may use clinician programmer 20 to program neurostimulation therapy for patient 12, as will be described in greater detail below.

System 10 also includes a patient programmer 26, which also may, as shown in FIG. 1, be a handheld computing device. Patient 12 may use patient programmer 26 to control the delivery of therapy by IMD 14. For example, using patient programmer 26, patient 12 may select a current neurostimulation therapy program or group of neurostimulation therapy programs from among the programs or program groups preprogrammed by the clinician, or may adjust one or more parameters of a therapy program or program group.

0049 Patient programmer 26 may also include a display 28 and a keypad 30 to allow patient 12 to interact with patient programmer 26. In some embodiments, display 28 may be a touch screen display, and patient 12 may interact with patient programmer 26 via display 28. Patient 12 may also interact with patient programmer 26 using peripheral pointing devices, such as a stylus, mouse, or the like.

However, clinician and patient programmers 20, 26 are not limited to the hand-held computer embodiments illustrated in FIG. 1. Programmers 20, 26 according to the invention may be any sort of computing device. For example, a programmer 20, 26 according to the invention may a tablet-based computing device, a desktop computing device, or a workstation.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using radio frequency (RF) telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

In some embodiments, the clinician may use clinician programmer 20 to create neurostimulation therapy programs. As part of the program creation process, clinician programmer 20 allows the clinician to identify electrode combinations that enable IMD 14 to deliver neurostimulation therapy that is desirable in terms of, for example, symptom relief, coverage area relative to symptom area, and side effects. Clinician programmer 20 may also allow the clinician to identify electrode combinations that enable IMD 14 to deliver effective neurostimulation therapy with desirable device performance characteristics, e.g., low battery consumption.

Clinician programmer 20 controls IMD 14 to test electrode combinations in order to allow a clinician to identify desirable combinations in an efficient manner. As will be described in greater detail below, clinician programmer 20 may select electrode combinations to test based on an electrode combination search algorithm. In particular, according to such an algorithm, clinician programmer 20 may first control IMD 14 to test one or more electrodes to identify the electrode which will act as a first cathode electrode, and then control IMD 14 to test combinations that include the first cathode in an order that is based on the proximity of other electrodes in the combination to the first cathode.

By controlling IMD 14 to test electrode combinations in such an order, clinician programmer 20 may allow the clinician to more quickly identify desirable electrode combinations, reducing the overall amount of time the clinician spends programming neurostimulation therapy for patient 12. In contrast to existing neurostimulation programming systems that present electrode combinations in a random order and idiosyncratic search methodologies employed by clinicians, clinician programmer 20 may select electrode combinations to test in an order such that electrode combinations that are more likely to enable desirable therapy are selected earlier in the search. Consequently, the clinician may be able to end the search before all potential electrode combinations have been tested if one or more desirable combinations have already been identified, saving the amount clinician and patient time required to achieve an efficacious electrode combination.

Even if the clinician elects to test all potential electrode combinations, e.g., if the electrode set is small enough to make testing all electrode combinations practical, programmer 20 may reduce the time required to identify desirable electrode combinations by automating selection of each new combination to test. Additionally, clinician programmer 20 may improve the search process by collecting amplitude and rating information for each combination tested. As will be described in greater detail below, clinician programmer 20 may present a list of electrode combinations to the clinician, ordered according to one or both of the amplitude and rating information, allowing the clinician to more easily identify and select desirable combinations.

After identifying a plurality of desirable electrode combinations, the clinician or patient 12 may use clinician programmer 20 to test variety of values of other neurostimulation therapy program parameters, such as pulse amplitude, pulse rate, pulse width and duty cycle, with the identified electrode combinations, i.e., to test a variety of neurostimulation therapy programs. Clinician programmer 20 may collect rating information, e.g., information relating to efficacy, power consumption and/or side effects, from patient 12 for each of the tested neurostimulation therapy programs. Based on this testing, the clinician may use clinician programmer 20 to identify a plurality of desirable neurostimulation therapy programs from among those tested during the programming session for use in controlling delivery of neurostimulation therapy to patient 12 by IMD 14.

In some embodiments, as will be described in greater detail below, clinician programmer 20 provides a neurostimulation therapy program replication function. In such embodiments, clinician programmer 20 selects one of the neurostimulation therapy programs identified during the programming session, e.g., receives a selection of one of the programs made by the clinician, and receives a replication command from the clinician. In response to the replication command, clinician programmer 20 generates one or more copies of the selected neurostimulation therapy program.

By replicating a neurostimulation therapy program that has been identified as desirable, clinician programmer 20 may allow a clinician to quickly generate a plurality of similarly desirable programs for selection and use by patient 12. In some embodiments, as part of generation of a copy, clinician programmer 20 may change one or more of the parameters of the selected program. For example, pulse amplitude, pulse width, pulse rate, duty cycle, or a combination thereof may be changed to provide a plurality of similar programs with various intensities and battery consumption rates. As an example, clinician programmer 20 may provide a "high intensity" and "low intensity" version of a selected program.

By providing a plurality of programs that are replicated with parameters that are changed in this manner, clinician programmer 20 may allow patient 12, to select a program that addresses a current symptom level, e.g., pain level which may vary based on patient posture, activity, or time of day, with a comparatively lower rate of battery consumption. In some embodiments, clinician programmer 20 may associate the selected program and the copies with respective postures, activities, times of day, symptom intensity states, or program side effect states, e.g., may label a selected program and a copy as "sitting" and "standing," "active" and "inactive," "daytime" and "nighttime," or "high" and "low," respectively.

In other embodiments, patient 12 may be unaware of the differences between the intensities of the program and the copies, and either IMD 14 or patient programmer 26 may collect information regarding the use of the program and the copies to determine whether patient 12 will accept a program with a lower intensity and battery consumption rate. In some embodiments, clinician programmer 20 may provide one or more copies that are identical to the selected program, and patient 12 may adjust one or more parameters of the copies to create similarly desirable programs with different intensities and battery consumption rates to, for example, address different symptom levels associated with different postures, activities, or times of day.

In some embodiments, IMD 14 delivers therapy to patient 12 according to program groups, i.e., groups of two or more neurostimulation therapy programs. IMD 14 may deliver the two or more programs of a program group to patient 12 substantially simultaneously. For example, IMD 14 may deliver each neurostimulation therapy pulse according to a different one of the plurality of programs of a program group.

In such embodiments, clinician programmer 20 may automatically generate one or more program groups that include two or more of a plurality of neurostimulation programs identified as desirable during programming session. In particular, clinician programmer 20 may associate each of a plurality of identified neurostimulation therapy programs with one or more of a plurality of program categories, and generate the groups, e.g., assign programs to groups, based on their associated program categories. Clinician programmer 20 may automatically generate the program groups in response to receiving a program group generation command from the clinician.

Each of the program categories is related to a characteristic of neurostimulation therapy programs. For example, clinician programmer 20 may categorize a neurostimulation therapy program by paresthesia location, e.g., left-side, right-side, or bilateral, or based on the location of electrodes included within its electrode combination. Generally, in embodiments in which neurostimulation therapy programs are categorized by paresthesia or electrode location, clinician programmer 20 may generate a program group to include programs associated with different categories, e.g., programs associated with different paresthesia or electrode locations. A program group that includes programs associated with different paresthesia or electrode locations may be able to, for example, address complex pain patterns, and avoid conflicts that can arise when sequential pulses are delivered according to different programs via the same electrodes.

As other examples, clinician programmer 20 may categorize a neurostimulation therapy program according stimulation intensity, e.g., high, medium or low, according to posture, e.g., standing or sitting, according to patient activity, e.g., running or sitting, according to time of day, e.g., daytime or evening, according to symptom intensity, e.g., high or low, or according to stimulation side effects, e.g., high or low. Generally, in embodiments in which neurostimulation therapy programs are categorized by intensity, posture, activity, time of day, symptom intensity, or side effects, clinician programmer 20 may generate a program group to include programs associated with same category, e.g., programs associated with same intensity, posture, activity, time of day, symptom intensity, or side effects. A program group that includes programs associated with same stimulation intensity level, symptom intensity level, posture, or activity, for example, may be selected by patient 12 to address a current symptom level, or when patient 12 assumes a particular posture or undertakes a particular activity.

In order to control IMD 14 to test electrode combinations and neurostimulation therapy programs, clinician programmer 20 may, as indicated above, communicate with IMD 14 via telemetry techniques known in the art. For example, clinician programmer 20 may communicate with IMD 14 via an RF telemetry head (not shown). Information identifying desirable combinations of electrodes identified by the clinician may be stored as part of neurostimulation therapy programs. Neurostimulation therapy programs, program copies, and/or program groups, created or generated as described above, may be transmitted to IMD 14 via telemetry, and/or may be transmitted to patient programmer 26 via any wired or wireless communication technique. Once stored by one or both of IMD 14 and programmer 26, the programs and/or program groups may be available for selection, e.g., by patient 12, to control delivery of therapy by IMD 14.

Figure 2:
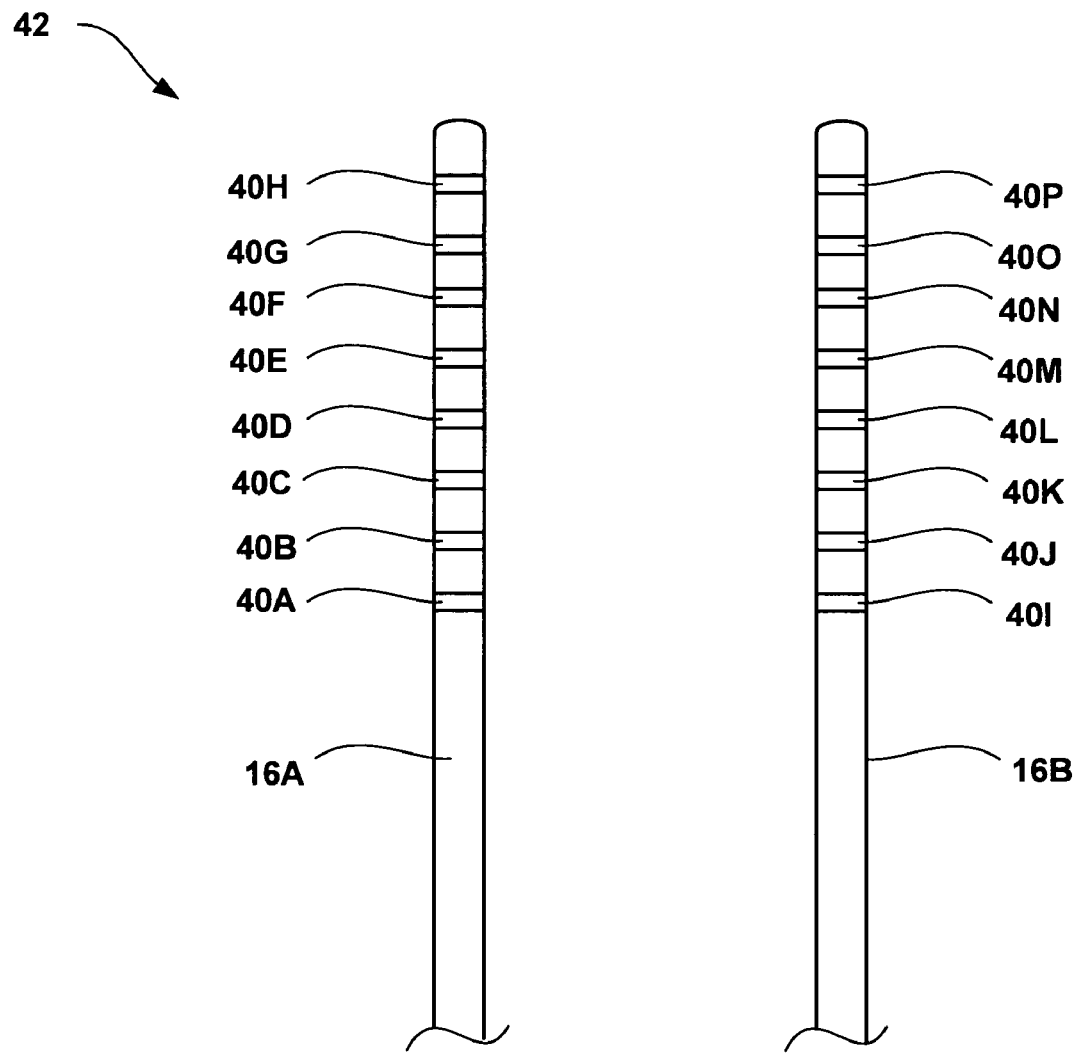
FIG. 2 is a diagram illustrating an example electrode set that may be implanted within the patient.

FIG. 2 is a block diagram illustrating an example configuration of leads 16. In the example configuration, lead 16A includes electrodes 40A-H, and lead 16B includes electrodes 40I-P. Electrodes 40A-P (collectively "electrodes 40") may be ring electrodes.

Electrodes 40 collectively form an electrode set 42 implanted within patient 12. As shown in FIG. 2, electrode set 42 includes eight electrodes on each of the two leads 16, which, as shown in FIG. 1, are implanted such that they are substantially parallel to each other and spinal cord 18, on substantially opposite sides of spinal cord 18, at approximately the same height relative to spinal cord 18, and oriented such that the distal ends of leads 16 are higher relative to the spinal cord than the proximal ends of leads 16. Therefore, the illustrated configuration of electrode set 42 may be described as a two-by-eight, side-by-side, upwardly oriented configuration.

Such a configuration is commonly used to provide SCS therapy. However, programmer 20 may be used to identify desirable combinations of electrodes within electrode sets that are configured in any way, and used to provide any type neurostimulation therapy. For example, a single lead including four or eight electrodes, two leads including four electrodes per lead, in-line leads, and offset leads, all of which may be oriented in any manner relative to patient 12, provide electrode set configurations that may be searched by programmer 20.

IMD 14 (FIG. 1) may deliver neurostimulation via any combination of electrodes 40. IMD 14 may independently activate each electrode 40 of set 42 to act as a cathode or anode for a combination, and each combination will include at least one cathode and at least one anode. In some embodiments, a combination may include a single electrode 40 acting as the cathode, with a can of IMD 14, i.e., the IMD housing, acting as the anode for the combination.

In an electrode combination, electrons flow from the one or more electrodes acting as anodes for the combination to the one or more electrodes acting as cathodes for the combination. The current between anodes and cathodes may stimulate neurons between and proximate to the anodes and cathodes. Generally speaking, an electrode combination enables desirable neurostimulation therapy when current is delivered in a direction and with an intensity sufficient to stimulate specific neurons or a sufficient number of specific neurons to alleviate a symptom without causing unacceptable side effects. Further, an electrode combination enables desirable neurostimulation therapy when the symptom is alleviated without resorting to undesirably high pulse amplitudes.

As mentioned above, clinician programmer 20 selects individual electrodes 40 or electrode combinations to test to allow a clinician to identify desirable electrode combinations according to an electrode search algorithm. Clinician programmer 20 may select an appropriate search algorithm based on the configuration of electrode set 42, and may select electrodes 40 or electrode combinations based on the selected search algorithm. Clinician programmer 20 controls IMD 14 to test a selected electrode 40 or electrode combination by controlling IMD 14 to deliver neurostimulation via the selected electrode 40 or combination.

Clinician programmer 20 may first control IMD 14 to test one or more of electrodes 40 individually to identify the individual electrode or electrodes 40 which will act as a first cathode. Generally, a clinician implants leads 16 in a location such that the center of electrode set 42 is proximate to an area that the clinician believes should be stimulated in order to alleviate symptoms. Therefore, clinician programmer 20 may test electrodes 40 as the first cathode in an order such that electrodes 40 located centrally within electrode set 42, e.g., electrodes 40D-E and 40L-M illustrated in FIG. 2, are tested before peripherally located electrodes. If the clinician's estimation of the target region is inaccurate, clinician programmer 20 will continue to test individual electrodes 40 in such an order until one of the electrodes 40 that enables desirable neurostimulation therapy when activated as the first cathode is identified. Initially locating a first cathode provides a "coarse" optimization of electrode combinations, allowing clinician programmer 20 and the clinician to quickly identify the general area to which neurostimulation therapy should be delivered.

Clinician programmer 20 may then control IMD 14 to test electrode combinations that include the first cathode. Clinician programmer 20 may control IMD 14 to try different ones of electrodes 40 as the first anode in a pair with the first cathode, and may add additional anodes and/or cathodes. Clinician programmer 20 may control IMD 14 to test remaining electrodes 40 as first anodes, and additional anodes or cathodes, in an order that is based on the proximity of the remaining electrodes 40 to the electrode 40 acting as the first cathode for the electrode combination. The order may be based on decreasing proximity of the remaining electrodes 40 to the electrode acting as the first cathode, e.g., electrodes will be tested in order of increasing distance from the first cathode.

Generally, electrode combinations that include cathodes and anodes in closer proximity may be more likely to enable desirable neurostimulation therapy. Therefore, by testing electrode combinations in an order based on decreasing proximity of the other electrodes 40, clinician programmer 20 provides a "fine" optimization of electrode combinations, allowing the clinician to more quickly identify electrode combinations that enable more desirable neurostimulation therapy than the initial combination including the first cathode and the first location of the first anode. With this approach, the search for electrode combinations may proceed in a pattern or "orbit" in close proximity about an initially selected cathode or cathodes, and then extend outward into a more distant orbit as the search continues.

Figure 3:
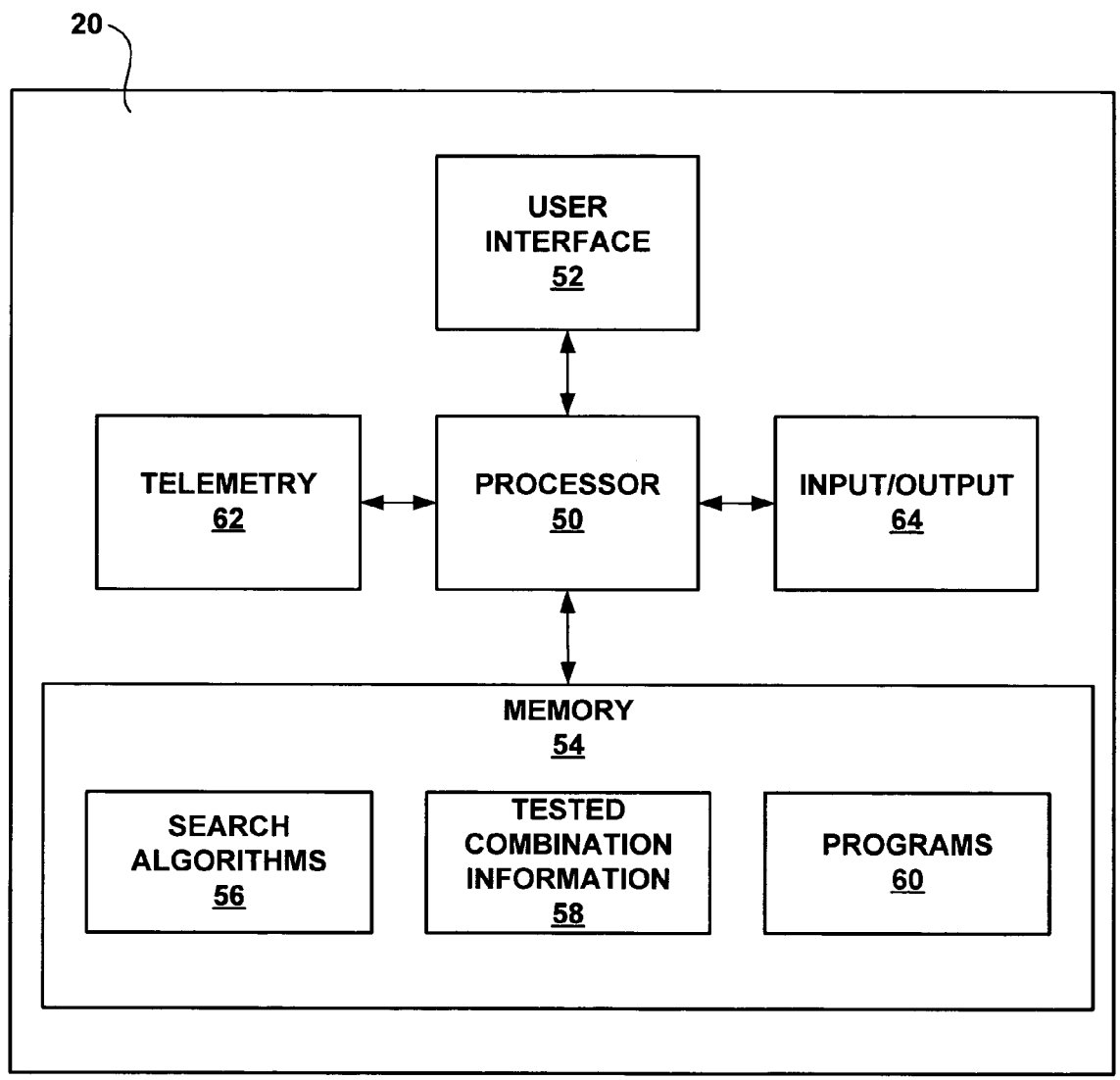
FIG. 3 is a block diagram illustrating an example programming device that allows a user to identify desirable electrode combinations for neurostimulation therapy programs.

FIG. 3 is a block diagram illustrating an example configuration of clinician programmer 20. A clinician may interact with a processor 50 via a user interface 52 in order to identify electrode combinations, identify neurostimulation therapy programs, request neurostimulation therapy program replication, and request automatic program group generation, as described herein. User interface 52 may include display 22 and keypad 24, and may also include a touch screen or peripheral pointing devices as described above. Processor 50 may also provide a graphical user interface (GUI) via user interface 52 to facilitate interaction with a clinician. Processor 50 may include a microprocessor, a controller, a digital signal processor (DSP), an application specific integrated circuit (ASIC), a field-programmable gate array (FPGA), discrete logic circuitry, or the like.

Clinician programmer 20 also includes a memory 54. Memory 54 may include program instructions that, when executed by processor 50, cause clinician programmer 20 to perform the functions ascribed to clinician programmer 20 herein. For example, processor 50 may execute a selected one of electrode combination search algorithms 56 stored within memory 54 to select individual electrodes 40 or electrode combinations to test to allow the clinician to identify desirable electrode combinations.

As will be described in greater detail below, processor 50 may collect information relating to tested electrode combinations, and store the information in memory 54 for later retrieval and review by the clinician to facilitate identification of desirable electrode combinations. Neurostimulation therapy programs 60 created by the clinician may be stored in memory 54, and information identifying electrode combinations selected by the clinician to be utilized for one of programs 60 may be stored as part of the program within memory 54. As described above, a plurality of desirable programs 60 may be identified, and may be replicated or assigned to program groups by processor 50. Memory 54 may include any volatile, non-volatile, fixed, removable, magnetic, optical, or electrical media, such as a random access memory (RAM), read-only memory (ROM), CD-ROM, hard disk, removable magnetic disk, memory cards or sticks, nonvolatile RAM (NVRAM), electrically-erasable programmable ROM (EEPROM), flash memory, and the like.

Processor 50 controls IMD 14 to test selected individual electrodes 40 or electrode combinations, by controlling IMD 14 to deliver neurostimulation therapy to patient 12 via the selected individual electrodes 40 or electrode combinations via a telemetry circuit 62. Similarly, processor 50 controls IMD 14 to test selected neurostimulation therapy programs 60, which include identified electrode combinations and other selected program parameters, by controlling IMD 14 to deliver neurostimulation therapy to patient 12 according to the selected program. Processor 50 may transmit programs 60 that are identified as desirable, copies of one or more such programs, and/or program groups that include two or more such programs to IMD 14 via telemetry circuit 62, or to patient programmer 26 via input/output circuitry 64. I/O circuitry 64 may include transceivers for wireless communication, appropriate ports for wired communication or communication via removable electrical media, or appropriate drives for communication via removable magnetic or optical media. Together, telemetry 62 and I/O circuitry 64 may form a communication circuit for clinician programmer 20.

Figure 4:
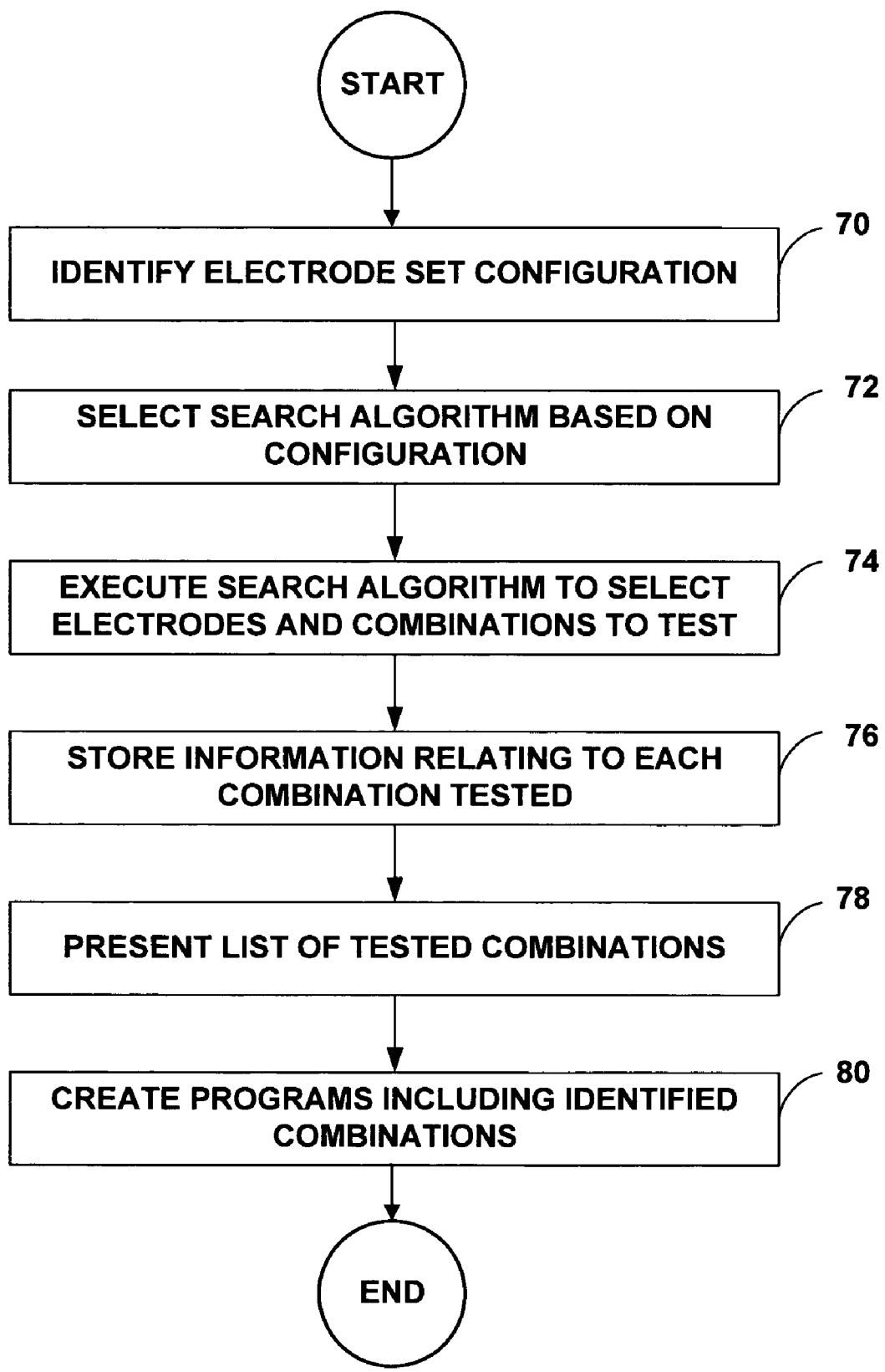
FIG. 4 is a flow diagram illustrating an example method that may be employed by a programming device to select and execute an electrode combination search algorithm according to the invention.

FIG. 4 is a flow diagram illustrating an example method that may be employed by clinician programmer 20 to select and execute an electrode combination search algorithm according to the invention. Clinician programmer 20, and more specifically processor 50 of clinician programmer 20, identifies a configuration of electrode set 42 (70), and selects an electrode combination search algorithm 56 based on the configuration (72). Multiple algorithms 56 may be available for selection in order to allow clinician programmer 20 to address differences between electrode configurations, e.g., different numbers of leads and electrodes per leads. However, each of algorithms 56 may employ the common search methodology that was discussed above, and is illustrated by FIGS. 5A and 5B discussed below.

Clinician programmer 20 may identify the configuration of electrode set 42 by, for example, receiving input from the clinician via user interface 52 indicating the configuration. In other embodiments, information identifying the configuration of electrode set 42 may be stored in memory 54 or a memory of IMD 14 at implant. In such embodiments, clinician programmer 20 may retrieve the information from memory 54 or from IMD 14 via telemetry circuit 62.

Clinician programmer 20 then, as will be described in greater detail below, executes the selected search algorithm to select individual electrodes 40 and electrode combinations to test (74). When a combination is tested, clinician programmer 20 may, as will also be described in greater detail below, store information 58 relating to that combination in memory 54. The information may include amplitude information, and/or rating information provided by one or both of the clinician and patient 12.

Clinician programmer 20 may present a list of tested combinations to the clinician via display 22 (78). The list may include the information relating to each combination, and in some embodiments, may be ordered according to information. The list may facilitate identification of one or more desirable electrode combinations by the clinician. The clinician may create neurostimulation therapy programs 60 that include identified electrode combinations (80), and clinician programmer 20 may store information identifying the electrode combinations selected by the clinician in memory 54, and use the selected combinations to generate programs 60. In some embodiments, clinician programmer 20 may automatically select electrode combinations for inclusion in programs 60 based on the information.

Figure 5A:
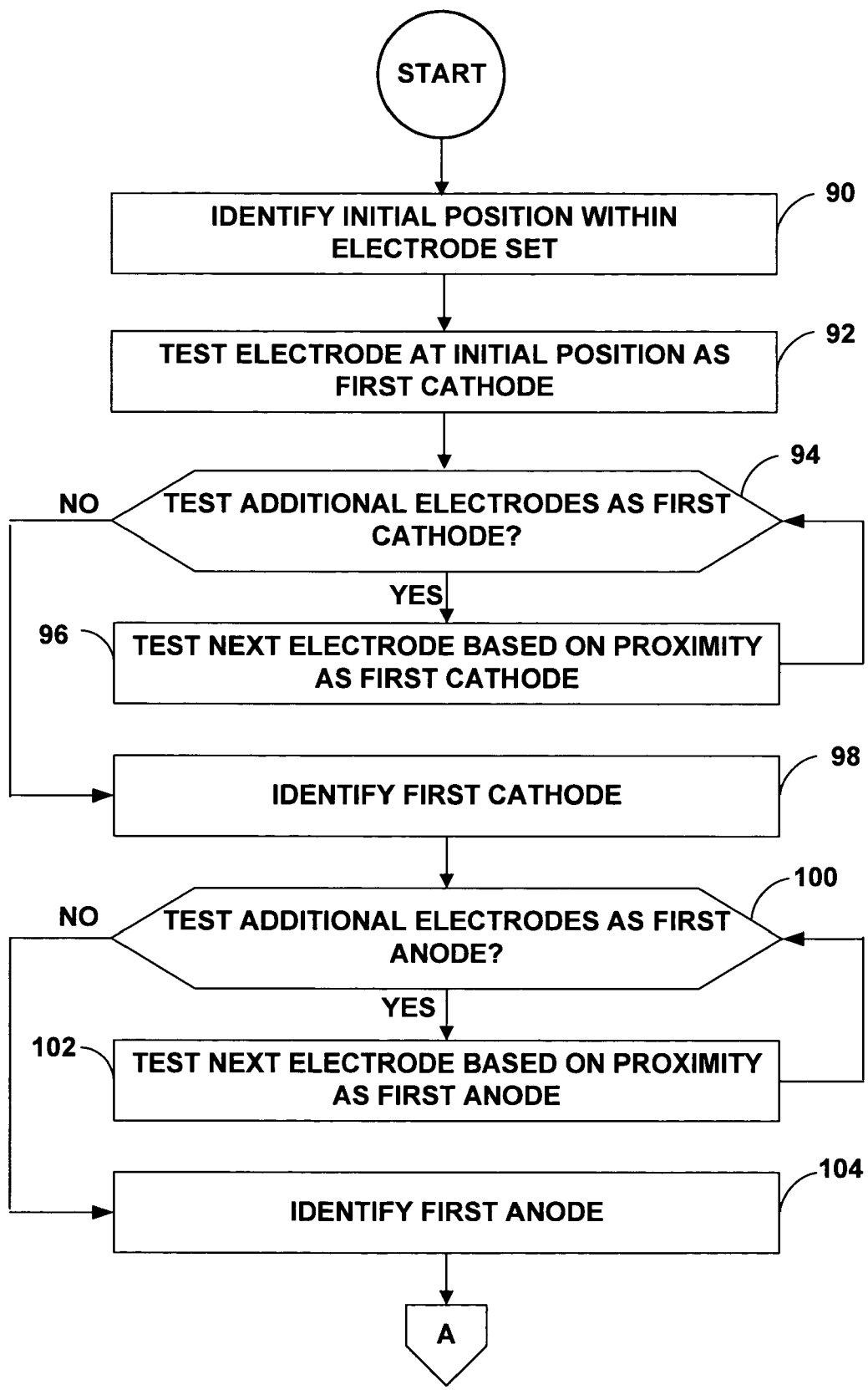
FIG. 5A and 5B are flow diagrams illustrating an example electrode combination search algorithm that may be executed by a programming device.
Figure 5B:
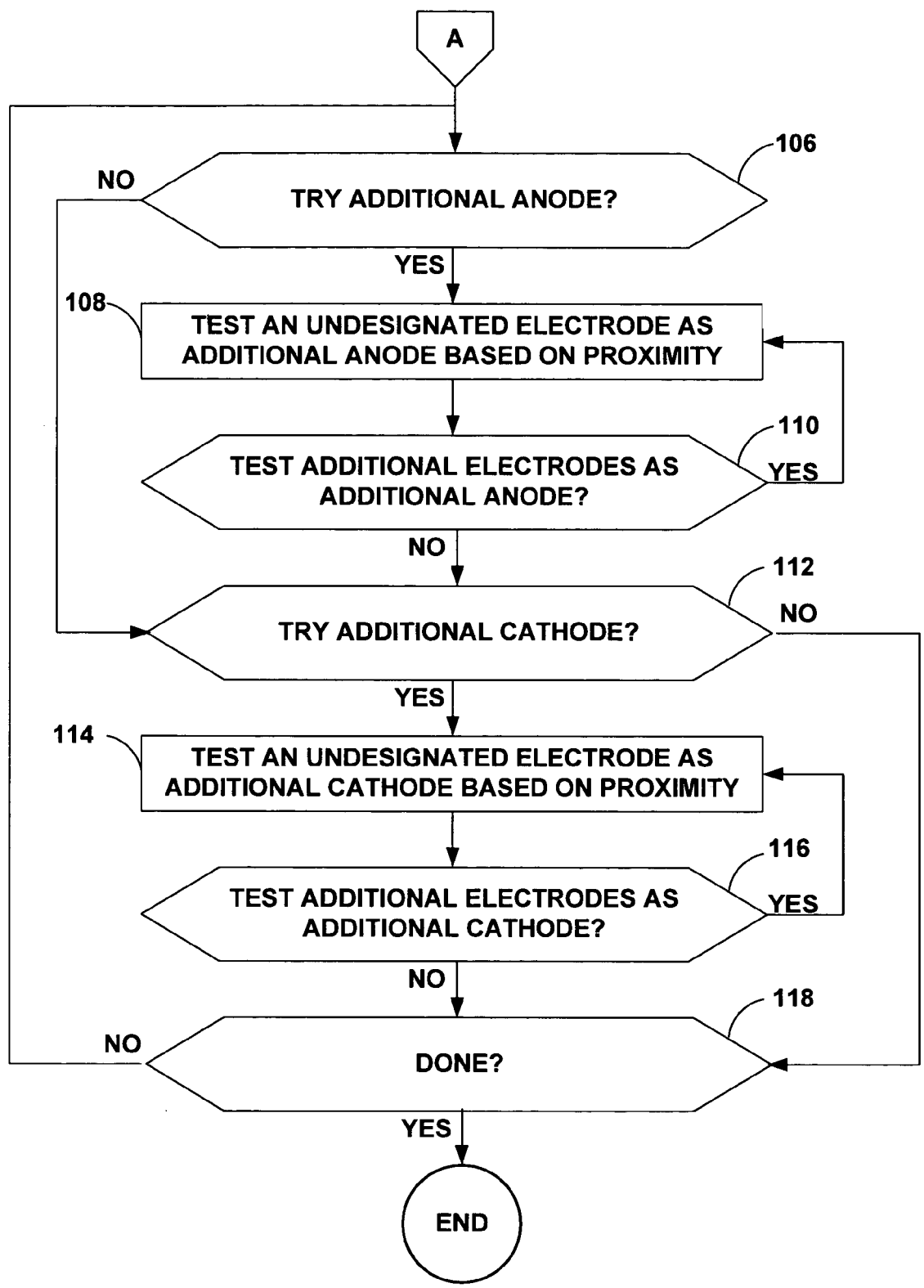

FIG. 5A and 5B are flow diagrams illustrating an example electrode combination search algorithm that may be executed by clinician programmer 20. As shown in FIG. 5A, clinician programmer 20 identifies an initial position within electrode set 42 (90), and controls IMD 14 to test an electrode 40 located at the initial position as the first cathode (92). As discussed above, the initial position may be a central position within electrode set 42, and programmer 20 may identify a central position within set 42 based on the configuration of set 42. For example, programmer 20 may initially control IMD 14 to test electrode 40E (FIG. 2) as the first cathode. Alternatively, the clinician may identify the initial position or the specific electrode 40 that the clinician believes should be tested first, and clinician programmer 20 may control IMD 14 to test the electrode 40 corresponding to input provided by the clinician.

Clinician programmer 20 then determines whether an additional electrode 40 should be tested as the first cathode (94). Clinician programmer 20 may prompt the clinician to indicate whether an additional electrode 40 should be tested. If the clinician is satisfied with the first electrode 40 tested, clinician programmer 20 identifies the first electrode as the first cathode for subsequently tested combinations (98). However, if the clinician indicates that additional electrodes 40 should be tested, clinician programmer 20 may control IMD 14 to test additional electrodes 40 of electrode set 42 in an order based on decreasing proximity to the initial position until the clinician indicates that no more electrodes 40 should be tested or all electrodes 40 of electrode set 42 have been tested (96). At that point, programmer 20 may identify the first cathode (98) either as the last electrode 40 tested, or based on input from the clinician identifying which of the tested electrodes 40 should be identified as the first cathode.

When clinician programmer 20 controls IMD 14 to test one of electrodes 40 as the first cathode, another one of electrodes 40 adjacent to the tested electrode, or the can of IMD 14, acts as a first anode to form a cathode/anode pair. When one of the tested electrodes 40 is identified as the first cathode (96), clinician programmer 20 may determine based on input received from the clinician whether other electrodes 40 of electrode set 42 are to be tested as the first anode (100). If the clinician indicates that no additional electrodes are to be tested as the first anode, programmer may identify the already tested electrode 40 adjacent to the first cathode as the first anode (104).

However, if the clinician indicates that additional electrodes 40 should be tested as the first anode, clinician programmer 20 may control IMD 14 to test additional electrodes 40 of electrode set 42 in an order based on decreasing proximity to the first cathode until the clinician indicates that no more electrodes 40 should be tested or all electrodes 40 of electrode set 42 have been tested (102). At that point, clinician programmer 20 may identify the first anode (104) either as the last electrode 40 tested, or based on input from the clinician identifying which of the tested electrodes 40 should be identified as the first anode. Each first cathode/first anode pair tested forms an electrode combination.

FIG. 5B illustrates portions of the example algorithm that enable programmer 20 and the clinician to try adding anodes and/or cathodes to the existing first cathode/first anode pair. In response to input from the clinician indicating that an additional anode or cathode should be added to an existing combination, programmer 20 selects electrodes to test as the additional anode or cathode. Where the existing combination is the first cathode/first anode pair, the resulting combinations tested may include guarded cathode or guarded anode combinations known in the art.

If clinician programmer 20 receives an indication to try an additional anode (106), programmer 20 controls IMD 14 to test undesignated electrodes 40 of electrode set 42 in an order based on decreasing proximity to the first cathode (108) until programmer 20 receives an indication to stop testing electrodes 40 or until all electrodes 40 of electrode set 42 have been tested (110). If clinician programmer 20 receives an indication to try an additional cathode (112), programmer 20 controls IMD 14 to test undesignated electrodes 40 of electrode set 42 in an order based on decreasing proximity to the first cathode (114) until programmer 20 receives an indication to stop testing electrodes 40 or until all electrodes 40 of electrode set 42 have been tested (116). After testing combinations that include the identified first cathode/first anode pair, and one or more additional anodes and/or one or more additional cathodes, clinician programmer 20 may select a different first anode or first cathode based on input received from the clinician. When the clinician is satisfied that desirable electrode combinations have been identified, or when all electrode combinations have been tested, clinician programmer 20 ends the electrode search algorithm (118), and may display a list of tested combinations as described above.

If the clinician stops the search before all possible combinations of electrodes 40 have been tested, clinician programmer 20 may create a bracket of untested combinations that the clinician may elect to include in neurostimulation therapy programs. The bracket may consist of any number of electrode combinations, and may comprise the next n combinations that would have been tested according to the electrode combination search algorithm. By providing the clinician with a bracket, clinician programmer 20 may allow clinician to spend less time searching for desirable electrode combinations. Specifically, the programs created using the bracket combinations may enable desirable neurostimulation therapy similar to that provided a program created with the most recently tested combination, and may be provided to patient 12 so that patient 12 can experiment with the bracket programs outside of the clinic.

FIGS. 6A-6K are diagrams illustrating example matrices 120-220 that illustrate positions within exemplary electrode sets. FIGS. 6A-B, D-E and H-J illustrate two-by-eight matrices 120, 130, 150, 160, 190, 200 and 210 that identify positions within a two-by-eight side-by-side electrode set, such as electrode set 42. FIGS. 6C, F-G and K illustrate one-by-eight matrices 140, 170, 180 and 220 that identify positions within a one-by-eight or two-by-four in-line electrode set. More particularly, FIGS. 6A-6K illustrate orders in which clinician programmer 20 may select electrodes within such electrode sets to test according to electrode combination search algorithms consistent with the invention, each position within a matrix indicating an electrode within an electrode set.

Matrices 120, 130 and 140 of FIGS. 6A-C illustrate orders in which clinician programmer 20 may select electrodes to test as the first cathode. The "–" symbol in each of matrices 120, 130 and 140 indicates the initial position, i.e., the first electrode tested as the first cathode. Additional electrodes may be tested as a first cathode in the numeric orders illustrated, which illustrate examples of testing orders that are based on decreasing proximity to the initial position.

Matrices 150, 160, 170 and 180 of FIGS. 6D-G illustrate orders in which clinician programmer 20 may select electrodes to test with an identified first cathode as the first anode. The "−" symbol in each of matrices 150, 160, 170 and 180 indicates the identified position of the first cathode. The "+" symbol in each of matrices 150, 160, 170 and 180 indicates the position of an electrode already tested with the first cathode as the first anode during the process of identifying the first cathode. Other electrodes of an electrode set corresponding to one of matrices 150, 160, 170 and 180 may be tested as a first anode in the numeric orders illustrated, which illustrate examples of testing orders that are based on decreasing proximity to the identified first cathode.

Matrices 190, 200, 210 and 220 of FIGS. 6H-K illustrate orders in which clinician programmer 20 may select electrodes to test with an identified first cathode/first anode pair as an additional anode. The "−" symbol in each of matrices 190, 200, 210 and 220 indicates the identified position of the first cathode. The "+" symbol in each of matrices 190, 200, 210 and 220 indicates the identified position of the first anode. Clinician programmer 20 may test other undesignated electrodes of an electrode set corresponding to one of matrices 190, 200, 210 and 220 as an additional anode in the numeric orders illustrated, which illustrate examples of testing orders that are based on decreasing proximity to the identified first cathode.

As illustrated by matrices 190, 210 and 220, clinician programmer 20 may test only a subset of the undesignated electrodes of an electrode set. Specifically, clinician programmer 20 may avoid testing electrodes as an additional anode that would provide substantially the same current flow as the first cathode/first anode pair due to the orientation of the additional anode and the first cathode/first anode pair. By testing only a subset of the undesignated electrodes and avoiding redundant combinations, clinician programmer 20 may further shorten the time required of the clinician to identify desirable electrode combinations.

The illustrated matrices are merely exemplary. Again, clinician programmer 20 may test electrodes within any type of electrode configuration. Further, configurations that include multiple additional anodes, or one or more additional cathodes may be tested. Whenever a cathode or anode is added, testing may be limited to a subset of undesignated electrodes in order to avoid redundant combinations.

Figure 7:
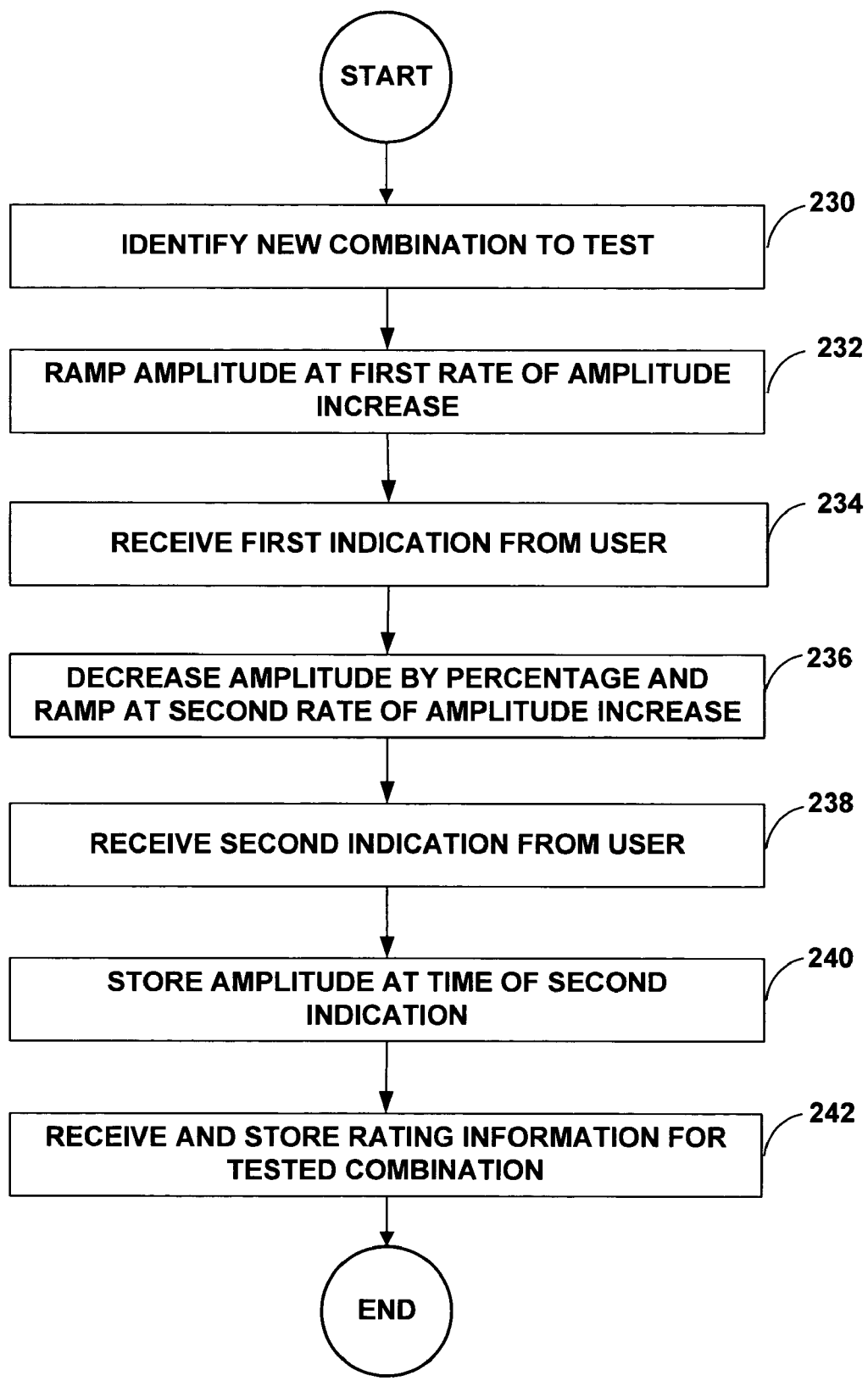
FIG. 7 is a flow diagram illustrating an example method that may be employed by a programming device to test an electrode combination according to the invention.

FIG. 7 is a flow diagram illustrating an example method that may be employed by clinician programmer 20 to test an electrode combination according to the invention. Specifically, FIG. 7 illustrates a method that may be employed by clinician programmer 20 each time a new electrode is tested as a first or additional cathode, or first or additional anode. In other words, FIG. 7 illustrates a method that may be employed by clinician programmer 20 each time clinician programmer 20 identifies a new electrode combination to test (230).

Clinician programmer 20 controls IMD 14 to test the combination by controlling IMD 14 to deliver neurostimulation therapy via the combination. The clinician may select desired starting points for pulse amplitude, rate and width, and clinician programmer 20 may ramp the amplitude from the starting point at a first rate of amplitude increase (232). Clinician programmer 20 may increase the amplitude in, for example, a linear or step-wise fashion. In some embodiments, the clinician or patient 12 may control the rate of amplitude increase.

The clinician or patient 12 stops the ramping of the amplitude when the stimulation causes discomfort, or other undesirable side effects (234).

Clinician programmer 20 may reduce the amplitude at the time the ramp is stopped by some amount, e.g., a percentage, and ramps the amplitude again in order to allow the clinician and/or patient 12 to identify the amplitude that provides the best neurostimulation therapy (236, 238). This second time, clinician programmer 20 may ramp the amplitude at a slower rate of amplitude increase in order to facilitate identification of the point where best neurostimulation is achieved. Again, in some embodiments, the clinician or patient 12 may control the amplitude.

Clinician programmer 20 stores the amplitude at the time when the best neurostimulation therapy is indicated by the clinician and/or patient 12, and rating information for the combination (240, 242). The clinician and/or patient 12 may provide rating information, e.g., a numerical value for one or more metrics for rating the combination, which relates to the efficacy enabled by the combination or the side effects resulting from use of the combination, or both.

The clinician may use rating information and/or the amplitude values stored for each tested combination to identify desirable combinations. The combinations and their associated information and values may be presented in a list that may be ordered according to the information, the values, or a combination of the two. The amplitude value may, for example, be used to distinguish between tested combinations with similar ratings based on the power that must be consumed in order for each combination to enable desirable neurostimulation therapy.

Figure 8:
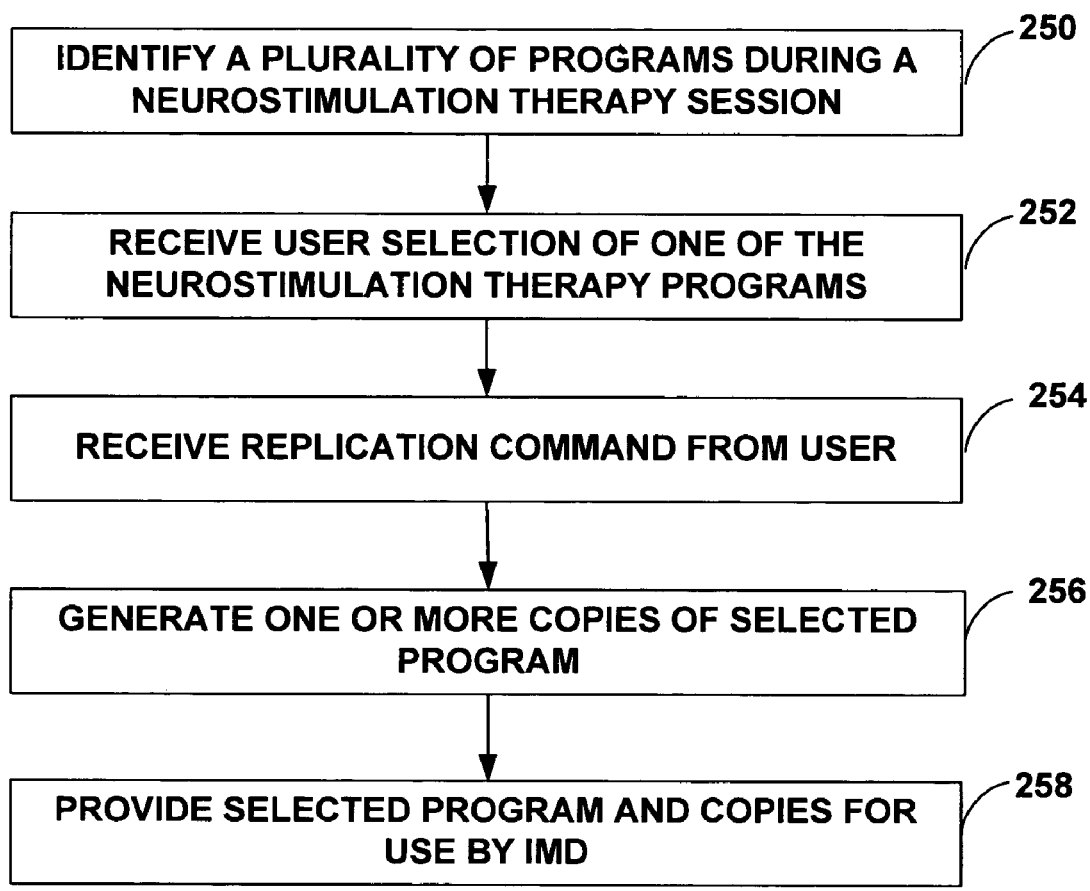
FIG. 8 is a flow diagram illustrating an example method that may be employed by a programming device to replicate a selected neurostimulation therapy program.

FIG. 8 is a flow diagram illustrating an example method that may be employed by clinician programmer 20 to replicate a selected neurostimulation therapy program. After identifying a plurality of desirable electrode combinations in the manner described above, the clinician or patient 12 may use clinician programmer 20 to test variety of values of other neurostimulation therapy program parameters, such as pulse amplitude, pulse rate, pulse width and duty cycle, with the identified electrode combinations, i.e., to test a variety of neurostimulation therapy programs 60. Clinician programmer 20 may collect rating information for each of the tested neurostimulation therapy programs, e.g., information indicating efficacy, side effects, or power consumption of each of the programs. Clinician programmer 20 identifies a plurality of desirable neurostimulation therapy programs 60 from among those tested during the programming session for use in controlling delivery of neurostimulation therapy to patient 12 by IMD 14, e.g., receives selections from among programs 60 made by the clinician via user interface 52 (250).

Clinician programmer 20 selects one of the neurostimulation therapy programs identified during the programming session, e.g., receives a selection of one of the programs made by the clinician, and receives a replication command from the clinician (252, 254). In response to the replication command, clinician programmer 20 generates one or more copies of the selected neurostimulation therapy program (256). Clinician programmer 20 provides the selected neurostimulation therapy program 60 and the one or more copies to at least one of IMD 14 and patient programmer 24, where they may be individually selected and used to control delivery of therapy by IMD 14 (258).

By replicating a neurostimulation therapy program that has been identified as desirable, clinician programmer 20 may allow a clinician to quickly generate a plurality of similarly desirable programs for selection and use by patient 12. In some embodiments, as part of generation of a copy (256), clinician programmer 20 may change one or more of the parameters of the selected program. For example, one or more of pulse amplitude, pulse width, pulse rate, or duty cycle may be changed to provide a plurality of similar programs with various intensities and battery consumption rates, e.g., clinician programmer may provide a "high intensity" and "low intensity" version of a selected program.

By providing a plurality of programs that are replicated with parameters that are changed in this manner, clinician programmer 20 may allow patient 12 to select a program that addresses a current symptom level, e.g., pain level which may vary based on patient posture, activity or time of day, with a comparatively lower rate of battery consumption. In some embodiments, clinician programmer 20 may associate the selected program and the copies with respective postures, activities, times of day, symptom intensity states, or program side effect states, e.g., may label a selected program and a copy as "sitting" and "standing," "active" and "inactive," "daytime" and "nighttime," or "high" and "low," respectively. In other embodiments, patient 12 may be unaware of the differences between the intensities of the program and the copies, and either IMD 14 or patient programmer 26 may collect information regarding the use of the program and the copies to determine whether patient 12 will accept a program with a lower intensity and battery consumption rate. In some embodiments, clinician programmer 20 may provide one or more copies that are identical to the selected program, and patient 12 may adjust one or more parameters of the copies to create similarly desirable programs with different intensities and battery consumption rates to, for example, address different symptom levels associated with different postures or activities.

Clinician programmer 20 may change one or more parameters of a program when creating a copy of the program by a user-selected amount or a predetermined amount. For example, in situations in which desirable programs are identified when patient 12 is in a sitting posture, clinician programmer 20 may generate a copy of at least one of the programs to be a "standing" version of the selected program. Clinician programmer 20 may change an intensity related parameter of the selected program, e.g., amplitude, by a predetermined amount that is substantially equal to the difference between an average pulse amplitude used by patients when sitting and an average pulse amplitude used by patients when standing. The predetermined amount may be determined experimentally, and may be stored in memory 54 such that it is available to processor 50.

As another example of a technique for generating one or more copies of a program by changing one or more parameters by a predetermined amount, clinician programmer 20 may generate a "high intensity" and/or a "low intensity" version of a program based on stimulation thresholds identified during the programming session. A pain threshold and a perception threshold are examples of stimulation thresholds that may be identified during a programming session. Clinician programmer 20 may identify the values of one or more intensity related program parameters, such as pulse amplitude and pulse width, that result in identification of these thresholds by patient 12, and may change parameter values when generating high intensity or low intensity copies of a program based on the parameter values associated with the thresholds. For example, clinician programmer 20 may generate a high intensity copy of a selected program such that one or more program parameter values of the copy are substantially equal to the values associated with a pain threshold, and may generate a low intensity copy of a selected program such that one or more program parameter values of the copy are substantially equal to the values associated with the perception threshold.

Figure 9:
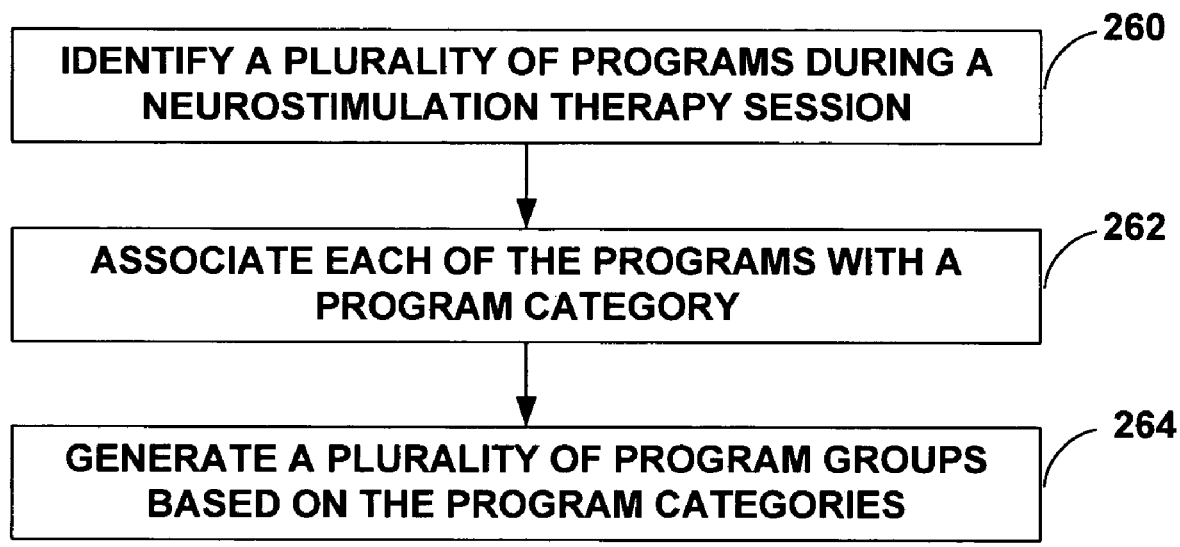
FIG. 9 is a flow diagram illustrating an example method that may be employed by a programming device to automatically generate program groups based on program categories associated with neurostimulation therapy programs.

FIG. 9 is a flow diagram illustrating an example method that may be employed by clinician programmer 20 to automatically generate program groups based on program categories associated with neurostimulation therapy programs. Clinician programmer 20 identifies a plurality of desirable neurostimulation therapy programs 60 from among those tested during a programming session, e.g., receives selections from among programs 60 made by the clinician via user interface 52 (260). Clinician programmer 20 then associates each of the plurality of identified neurostimulation therapy programs with one or more of a plurality of program categories (262), and automatically generates a plurality of program groups, e.g., automatically assigns programs to groups, based on their associated program categories (262, 264). Clinician programmer 20, as indicated above, may automatically generate the program groups in response to receiving a program group generation command from the clinician via user interface 52.

As indicated above, each of the program categories is related to a characteristic of neurostimulation therapy programs. Clinician programmer 20 may generate program groups to include programs associated with different categories, e.g., programs associated with different paresthesia or electrode locations, or may generate program groups to include programs associated with same category, e.g., programs associated with same intensity or same posture. In exemplary embodiments, clinician programmer 20 combinatorially generates program groups from a set neurostimulation therapy programs identified during a programming session. In other words, clinician programmer 20 may automatically generate a plurality of program groups by generating multiple combinations of neurostimulation therapy programs that comply with one or more criteria related to program categories. In some embodiments, clinician programmer 20 may order the programs within each category according to rating information, e.g., collected during a neurostimulation programming session, and may maintain a preference for use of more "highly" rated programs when combining programs to create groups, e.g., may create program groups based on both the program categories and the rating information. For example, clinician programmer 20 may exclude "poorly" rated programs from program groups, or may assign higher rated programs to groups more frequently than lower rated programs.

Various embodiments of the invention have been described. However, one skilled in the art will appreciate that various additions and modifications can be made to these embodiments without departing from the scope of the invention. For example, although programmer 20 has been described herein as a hand-held computing device, clinician programmer 20 may take the form of any type of computing device, such as a laptop or desktop computer, may access resources, such as memory 54, via a computer network, such as a LAN, WAN, or the World Wide Web. Further, clinician programmer 20 may include a plurality of computing devices, which may communicate to provide the functionality ascribed to clinician programmer 20 herein via a computer network.

Although described herein as associated with and interacting with a clinician, clinician programmer 20 may additionally or alternatively be associated with patient 12, i.e., act as a patient programmer. In some embodiments, patient 12 may simply interact with programmer 20 in place of the clinician for some or all of the electrode combination and neurostimulation therapy program identification process. In other embodiments, patient 12 may perform parts of the combination identification process without being supervised by the clinician, e.g., away from the clinic, using patient programmer 26.

Additionally, neurostimulation programs selected for replication and/or combination into program groups need not be programs identified during a neurostimulation programming session. For example, programs retrieved from a trial neurostimulator or patient programmer 26, such as programs that are the result of patient adjustment parameters over a trialing period, may be replicated and/or combined into program groups. Similarly, programs may be retrieved from IMD 14 or patient programmer 26 during a follow up visit, and selected for replication and/or program group generation based on usage or rating information stored by IMD 14 or patient programmer 26. Further, the clinician may store neurostimulation therapy programs that have been identified as generally efficacious, e.g., during treatment of other patients, in memory 56 or another memory accessible by clinician programmer 20, and may select such programs for replication and/or combination into program groups. These and other embodiments are within the scope of the following claims.

The invention claimed is:

1. A method comprising:
   selecting a neurostimulation therapy program that includes a set of neurostimulation therapy parameters;
   receiving a replication command from a user;
   automatically generating a copy of the selected neurostimulation therapy program in response to the replication command, wherein automatically generating a copy comprises automatically generating the copy with a value of at least one of the neurostimulation therapy parameters modified relative to a value of the neurostimulation therapy parameter for the selected program in response to the command; and
   providing the selected neurostimulation therapy program and the copy to at least one of a programming device or a medical device, wherein a selected one or more of the neurostimulation therapy program and the copy controls delivery of neurostimulation therapy to a patient by the medical device.

2. The method of claim 1, wherein the modified neurostimulation therapy parameter value comprises an amplitude of the selected neurostimulation therapy program.

3. The method of claim 1, wherein the modified neurostimulation therapy parameter value comprises a duty cycle of the selected neurostimulation therapy program.

4. The method of claim 1, wherein automatically generating the copy with a value of at least one of the neurostimulation therapy parameters modified relative to a value of the neurostimulation therapy parameter for the selected program comprises changing the neurostimulation therapy parameter value by an amount selected by the user.

5. The method of claim 1, wherein automatically generating the copy with a value of at least one of the neurostimulation therapy parameters modified relative to a value of the neurostimulation therapy parameter for the selected program comprises changing the neurostimulation therapy parameter value by a predetermined amount.

6. The method of claim 1, wherein automatically generating a copy comprises at least one of automatically generating a copy that provides a higher neurostimulation intensity relative to the selected neurostimulation therapy program or automatically generating a copy that provides a lower neurostimulation intensity relative to the selected neurostimulation therapy program.

7. The method of claim 6, wherein automatically generating a copy that provides a higher neurostimulation intensity comprises generating the copy with an amplitude approximately equal to a previously determined pain threshold of the patient, and automatically generating a copy that provides a lower neurostimulation intensity comprises generating the copy with the amplitude approximately equal to a previously determined perception threshold of the patient.

8. The method of claim 1,
   wherein automatically generating a copy of the selected neurostimulation therapy program comprises automatically generating a plurality of copies of the selected neurostimulation therapy program, each of the copies having a respective value of the neurostimulation therapy parameter that is modified relative to the value of the neurostimulation therapy parameter for the selected program, in response to the replication command, and
   wherein providing the selected neurostimulation therapy program and the copy to at least one of a programming device or a medical device comprises providing the selected neurostimulation therapy program and the plurality of copies to at least one of the programming device or the medical device.

9. The method of claim 1, wherein providing the selected neurostimulation therapy program and the copy to at least one of a programming device or a medical device comprises:
   including the selected neurostimulation therapy program in a first program group that includes one or more neurostimulation therapy programs;
   including the copy in a second program group that includes one or more neurostimulation therapy programs; and
   providing the first and second program groups to at least one of the programming device or the medical device, wherein a selected one of the first and second groups controls delivery of neurostimulation therapy to the patient by the medical device.

10. The method of claim 1, further comprising associating the selected neurostimulation therapy program and the copy with at least one of respective patient postures or respective patient activities.

11. The method of claim 1, further comprising associating the selected neurostimulation therapy program and the copy with respective times of day.

12. The method of claim 1, further comprising associating the selected neurostimulation therapy program and the copy with at least one of respective symptom states or respective side effect states.

13. The method of claim 1, wherein selecting a neurostimulation therapy program comprises selecting one of a plurality of neurostimulation therapy programs identified during a programming session.

14. The method of claim 1, wherein selecting a neurostimulation therapy program comprises receiving a selection of the neurostimulation therapy program by the user.

15. A device comprising:
   a user interface;
   a communication circuit; and
   a processor to select a neurostimulation therapy program that includes a set of neurostimulation therapy parameters, receive a replication command from a user via the user interface, automatically generate a copy of the selected neurostimulation therapy program in response to the replication command, and provide the selected neurostimulation therapy program and the copy to at least one of a programming device or a medical device via the communication circuit, wherein a selected one or more of the neurostimulation therapy program and the copy controls delivery of neurostimulation therapy to a patient by the medical device, and wherein the processor automatically generates the copy with a value of at least one of the neurostimulation therapy parameters modified relative to a value of the neurostimulation therapy parameter for the selected program in response to the replication command.

16. The device of claim 15, wherein the processor automatically generates the copy with an amplitude modified relative to an amplitude of the selected neurostimulation therapy program.

17. The device of claim 15, wherein the processor automatically generates the copy with a duty cycle modified relative to a duty cycle of the selected neurostimulation therapy program.

18. The device of claim 15, wherein the processor changes the parameter value by an amount selected by the user when generating the copy.

19. The device of claim 15, wherein the processor changes the parameter value by a predetermined amount when generating the copy.

20. The device of claim 15, wherein the processor automatically generates at least one of a copy that provides a higher neurostimulation intensity relative to the selected neurostimulation therapy program or a copy that provides a lower neurostimulation intensity relative to the selected neurostimulation therapy program.

21. The device of claim 20, wherein the copy that provides a higher neurostimulation intensity includes an amplitude approximately equal to a previously determined pain threshold of the patient, and the copy that provides a lower neurostimulation includes an amplitude approximately equal to a perception threshold of the patient.

22. The device of claim 15, wherein the processor automatically generates a plurality of copies of the selected neurostimulation therapy program, each of the copies having a respective value of the neurostimulation therapy parameter that is modified relative to the value of the neurostimulation therapy parameter for the selected program, in response to the replication command, and provides the selected neurostimulation therapy program and the plurality of copies to at least one of the programming device or the medical device via the communication circuit.

23. The device of claim 15,
wherein the processor includes the selected neurostimulation therapy program in a first program group that includes one or more neurostimulation therapy programs, includes the copy in a second program group that includes one or more neurostimulation therapy programs, and provides the first and second program groups to at least one of the programming device or the medical device, and
wherein a selected one of the first and second groups controls delivery of neurostimulation therapy to the patient by the medical device.

24. The device of claim 15, wherein the processor associates the selected neurostimulation therapy program and the copy with at least one of respective patient postures or respective patient activities.

25. The device of claim 15, wherein the processor associates the selected neurostimulation therapy program and the copy with respective times of day.

26. The device of claim 15, wherein the processor associates the selected neurostimulation therapy program and the copy with at least one of respective symptom states or respective side effect states.

27. The device of claim 15, wherein the selected neurostimulation therapy program is one of a plurality of neurostimulation therapy programs identified during a programming session.

28. The device of claim 15, wherein the processor receives a selection of the neurostimulation therapy program made by the user via the user interface.

29. A computer-readable medium comprising instructions that cause a programmable processor to:
select a neurostimulation therapy program that includes a set of neurostimulation therapy parameters;
receive a replication command from a user;
automatically generate a copy of the selected neurostimulation therapy program in response to the replication command; and
provide the selected neurostimulation therapy program and the copy to at least one of a programming device or a medical device,
wherein a selected one or more of the neurostimulation therapy program and the copy controls delivery of neurostimulation therapy to a patient by the medical device, and
wherein the instructions that cause a programmable processor to automatically generate a copy comprises instructions that cause the programmable processor to automatically generate the copy with a value of at least one of the neurostimulation therapy parameters modified relative to a value of the neurostimulation therapy parameter for the selected program in response to the replication command.

30. The computer-readable medium of claim 29,
wherein the instructions that cause the programmable processor to automatically generate a copy of the selected neurostimulation therapy program comprise instructions that cause the programmable processor to automatically generate a plurality of copies of the selected neurostimulation therapy program in response to the replication command, each of the copies having a respective value of the neurostimulation therapy parameter that is modified relative to the value of neurostimulation parameter for the selected program, and
wherein the instructions that cause a programmable processor to provide the selected neurostimulation therapy program and the copy to at least one of a programming device or a medical device comprise instructions that cause the programmable processor to provide the selected neurostimulation therapy program and the plurality of copies to at least one of the programming device or the medical device.

31. The computer-readable medium of claim 29, wherein the instructions that cause the programmable processor to provide the selected neurostimulation therapy program and the copy to at least one of a programming device or a medical device comprise instructions that cause a programmable processor to:
include the selected neurostimulation therapy program in a first program group that includes one or more neurostimulation therapy programs;
include the copy in a second program group that includes one or more neurostimulation therapy programs; and
provide the first and second program groups to at least one of the programming device or the medical device, wherein a selected one of the first and second groups controls delivery of neurostimulation therapy to the patient by the medical device.

* * * * *